United States Patent [19]

Lemelson

[11] Patent Number: 5,181,521
[45] Date of Patent: Jan. 26, 1993

[54] PORTABLE ELECTRONIC INSTRUMENT AND METHOD

[76] Inventor: Jerome H. Lemelson, Suite 286, 930 Tahoe Blvd, Unit 802, Princeton, N.J. 89451-9436

[21] Appl. No.: 117,809

[22] Filed: Nov. 6, 1987

Related U.S. Application Data

[63] Continuation of Ser. No. 841,888, Mar. 20, 1986, abandoned.

[51] Int. Cl.$^5$ .............................................. A61B 5/02
[52] U.S. Cl. .................................................. 128/736
[58] Field of Search ............... 128/639, 662, 663, 670, 128/687, 689–691, 711, 736; 374/142, 170, 186; 364/557, 418

[56] References Cited

U.S. PATENT DOCUMENTS

| | | | |
|---|---|---|---|
| 3,572,316 | 3/1971 | Vogelman et al. | 128/690 |
| 3,651,694 | 3/1972 | Lamb | 128/736 |
| 3,916,877 | 11/1975 | Beckman | 128/670 |
| 3,996,928 | 12/1976 | Marx | 128/736 |
| 4,033,336 | 7/1977 | Murawski et al. | 128/711 |
| 4,053,951 | 10/1977 | Hudspeth et al. | 128/736 |
| 4,055,166 | 10/1977 | Simpson et al. | 128/736 |
| 4,116,228 | 9/1978 | Hudspeth et al. | 128/736 |
| 4,121,574 | 10/1978 | Lester | 128/689 |
| 4,129,125 | 12/1978 | Lester et al. | 128/736 |
| 4,183,354 | 1/1980 | Sibley et al. | 128/711 |
| 4,403,605 | 9/1983 | Tanikawa | 128/6 |
| 4,407,295 | 10/1983 | Steuer et al. | 128/736 |
| 4,428,685 | 1/1984 | Lemelson et al. | 128/736 |
| 4,450,843 | 5/1984 | Barney et al. | 128/670 |
| 4,498,481 | 2/1985 | Lemke | 128/736 |
| 4,503,862 | 3/1985 | Baessler | 128/736 |

OTHER PUBLICATIONS

"A Portable Physiological Data Recording/Decoding System" by Hoodless et al., Biomed. Eng. vol. 2, No. 3 Jul. 1980, pp. 193–196.

Primary Examiner—David M. Shay
Attorney, Agent, or Firm—Steven G. Lisa

[57] ABSTRACT

An electronic thermometer and a method for sensing, indicating and recording temperatures of one or more living beings such as patients in a hospital. In a preferred form, the instrument is portable and contains on-board means for selectively reproducing signals defining past temperatures made of an individual and applying same to a visual display, a printer and/or an external memory such as associated with a master or storage computer for a medical facility or hospital. The playback control includes means such as a keyboard or series of switches, for reproducing just those temperature signals which were generated when a select person's temperature was taken over a select period of time to the exclusion of other signals recorded in the instrument's memory. Auxilliary subsystems may include a microphone and recorder of speech signals indicative of the identity of the person whose temperature is measured, a light pen or other means for generating and recording signals indicative of the identity of the persons whose temperatures are sensed, a speaker for generating sounds of synthetic or recorded speech indicative of temperatures taken and the persons whose temperatures are taken, time and date signal generating and indicating means, etc. The instrument also includes inputs for transducers for sensing other variables such as heartbeat and electronic circuitry for receiving signals from such sensors and calculating one or more physiological variables to be recorded and displayed.

1 Claim, 2 Drawing Sheets

PORTABLE ELECTRONIC INSTRUMENT AND METHOD

RELATED APPLICATIONS

This is a continuation of application Ser. No. 841,888 filed Mar. 20, 1986.

FIELD OF THE INVENTION

The invention is in the field of temperature measurement instrumentation, recording and indication, particularly of the portable type which may be used by medical personnel to measure or sense record and playback signals and display indications of body temperature of one or more persons taken at different time intervals over a period of time.

THE PRIOR ART

The prior art consists of portable electrical and electronic thermometers which sense and display temperature, such as body temperature, when it is taken. Such portable temperature indicating devices are exemplified by U.S. Pat. No. 4,428,685 and the references cited therein as well as other issued patents and merely serve to take and indicate by means of a display a temperature as it is taken. Such patent also teaches electronic means for indicating temperatures, as they are taken, by means of synthetic speech. U.S. Pat. No. 4,286,465 discloses an electronic system for periodically recording temperatures of an environment under timer control for the purpose of calculating temperature extremes. U.S. Pat. No. 4,397,569 entitled System for Correlating a Signal Sensor Location with a Recorder Printout employs a remote multiple point recorder and a system for correlating condition indicating signals fed sequentially from a series of sensors, such as used to sense temperatures of a machine or klin. These devices and systems suffer numerous shortcomings which render them incapable of performing functions relating to the measurement and recording of body temperatures of a plurality of individuals or patients and the indentification of the temperatures and patients whose temperatures were taken.

Other U.S. Patents exemplifying the prior art include U.S. Pat. No. 4,053,951 entitled Data Acquisition, Storage and Dispaly System; U.S. Pat. No. 4,121,574 entiled Method and Apparatus for Measuring and Recording Vital Signs of a Patient and U.S. Pat. No. 4,569,355 entitled Method and Apparatus for Monitoring and Diagnosing Peripheral Blood Flow. All require a plurality of separate sensing and data processing units connected or connectable by plugging the units together to permit data to be transferred therebetween and displayed or processed.

DESCRIPTION OF THE PRIOR ART

The prior art consists of body temperature taking and recording devices and systems employing electronic processing of signals generated by temperature sensing elements and electrical signal driven displays, such as liquid crystal numerical displays, which display numerical indications of the temperature taken after the sensing element has stabilized or terminates its variation in temperature indicating signal. These prior art devices and systems vary from hand-held units which indicate temperature per se to hand-held units which sense and record signals indicative of temperatures taken as well as other data, and which display each temperature as it is taken and prior to recording same U.S. Pat. No. 4,121,574 discloses a method and apparatus for measuring and recording vital signs of a living being using a portable housing connected by cable to a thermometer. However, a separate computer console is required, to which the portable unit is electrically coupled, to indicate and print charts of past temperatures taken of a patient over a period of time. U.S. Pat. No. 4,053,951 discloses a data aquisition and storage system for use in sensing and recording temperatures and other physiological variables of patients. Like the '574 patent, a separate console to which a portable hand-held unit is coupleable, is employed to display and print past temperatures and identify the persons who physiological variables were sensed and recorded in the portable unit. U.S. Pat. No. 4,569,355 relates to a method and apparatus for monitoring and diagnosing peripheral blood flow employing an artificial change in temperature of the skin using a coolant. A sensor of a monitor device is applied against the skin and a portable printer is coupled thereto which displays and prints each temperature taken. Keys of the printer unit are used to program and operate the printer and to enter variable data to be printed. Other patents disclosing electronic devices which take and display temperatures as they are sensed include U.S. Pat. Nos. 4,428,685; 4,286,465 and 4,397,569.

SUMMARY OF THE INVENTION

This invention relates to a system and method for indicating and recording temperature. In a particular form, the invention relates to a portable temperature indicating and recording-arrangement wherein temperature taken along with time including the time of day and date are recorded in the form of codes and/or characters. In one form, where the thermometer is employed to take and effect the recording of temperatures of a living being, it is provided with a small printer, such as a hand-held thermal printer or an ink jet printer, connected to the thermometer by means of a flexible cable and containing a pluggable memory which may be removed and applied to a communication network or computer for communicating and recording the data recorded therein for the purpose of diagnosis and further record keeping. Such printer also contains a keyboard for entering data identifying the patient and, in certain instances, the physician in charge of the patient to permit the temperature and time data to be properly entered into a computer and transmitted to a terminal or memory of the physician. In another form, a microphone is supported by the housing of the printer and its output signals are applied to speech signal processor and recorder for recording speech information directed into the microphone, such as the name or identification number of the person whose temperature is being recorded. In yet another form, the output of such microphone is applied to a microelectronic speech recognition computer for recognizing selected words of speech, such as the name or names of the patient, room and bed number or other information wherein the computer generates output control signals for controlling the operation of a code generating memory to cause it to generate a code associated with the patient and to either record such code in a memory in which temperature and time signals are also recorded and/or to operate the printing mechanism of the device or an auxilliary printer, to cause it to print the patient's or subject's name together with characters defining the name or identification of the patient on a sheet or strip of paper. The portable device may also be provided with an attached or cable connected light-pen for generating patient identifying codes recorded on tags, sheets and the like when the pen or thermometer is hand held and caused to scan such printed code. In a particular form, the medical instrument and recorder is also provided with an on-board or cable connected microphone or pressure sensor for sensing blood pressure pulse or sounds indicative of heart beat while the electronic circuitry of the device calculates and records heart beat rate, time of day and, in certain instances, date and patient identification codes.

Accordingly it is a primary object of this invention to provide a new and improved temperature measuring and indicating device and method for measuring and recording body temperatures of one or more individuals such as patients.

Another object is to provide an electronic system and method for sensing physiological variables of a plurality of different living beings, recording the results along with data identifying the living beings whose variables are sensed and data indicative of the times such variables were sensed.

Another object is to provide a portable thermometer for use in a hospital to measure and record temperatures of a plurality of patients, wherein recording is effected in a manner to eliminate the need of a nurse or medical attendant to manually write same on a chart.

Another object is to provide a new and improved portable physiological parameter measuring and recording device which may be used in hospitals and the like to measure and record one or more physiological variables.

Another object is to provide a physiological variable indicating device and electronic control system employing a magnetic tape recorder of data or speech signals defined by words spoken into a microphone which identify persons whose variables are sensed and measured, wherein recording of a plurality of measurement and signals of corresponding speech is effected.

Another object is to provide a measurement and recording system for physiological variables of a plurality of patients in a hospital, which system is portable and permits variables of many patients to be sensed and recorded in a manner to be easily accessible thereafter by a computer for use by physicians.

Another object is to provide a portable electronic thermometer for measuring and recording temperatures of a plurality of patients together with the signals indicative of the times such temperatures were taken and other signals indicative of the identities of the patients whose temperatures were taken wherein such operations are effected with minimum labor and effort required.

Another object is to provide a portable recording thermometer with an attendant light pen scanner for generating patient identifying codes before or after each temperature is measured and recorded in a memory thereof to identify, for later reference, the patients whose temperatures are sensed and recorded.

Another object is to provide a device and method for simultaneously sensing both temperature and heart beat of a living being.

Another object is to provide a medical instrument which is operable to sense and record or display both body temperature and heart or pulse rate of a living being either simultaneously and/or sequentially wherein both temperature and pulse or body sound sensors are supported adjacent to each other on a common mount and are simultaneously applied to the skin of the subject.

With the above and such other objects in view as will hereinafter more fully appear, the invention consists of the novel constructions, combinations and arrangements of parts and electrical components as will be more fully described and illustrated in the accompanying drawings, but it is to be understood that changes, variations and modifications may be resorted to which fall within the scope of the invention as claimed.

Figure 1:
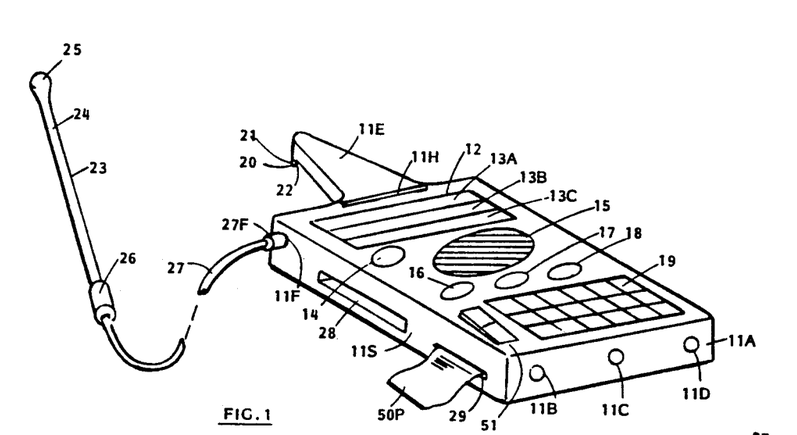
FIG. 1 is an isometric view of a portable thermometer which includes recording means for signals indicative of temperatures sensed, times and dates on which such temperatures are sensed and recorded and patient identifying signals as well as auxilliary measuring and recording means.

In FIG. 1 is shown a portable electronic instrument 10 for measuring and recording one or more physiological variables such as body temperature, heart or pulse rate, etc. and for providing such information in one or more forms such as a visual display thereof or in coded form for transmission to and use by a computer remote from the instrument. Housing 11 supports an electrically operated display 12, which is shown as having a plurality of display lines 13a, 13b and 13c for variable characters such/as numerical characters with or without alphabetical characters. Such display may be of the light emitting diode (LED) or liquid crystal (LCD) type or a combination of same and may be employed to display both current data as it is generated and past data generated from a memory or recorder as will be described.

Also mounted on and supported by the housing 11 are a microphone 14, a speaker 15, a plurality of manual control switches 16, 17 and 18 and a manually operable keyboard 19 contain a plurality of coded push-button or pressure operated manual switches. Housing 11 is illustrated as a flat rectangular parallelepiped enclosure and contains a protruding extension 11E of narrow-tapered configuration which extension supports an electro-optical sensing assembly 20 which includes a photoelectric cell and a light source, denoted 21 and 22, in a suitable optical assembly for scanning printed matter such as bar codes for identifying patients and generating other data to be recorded along with physiological data of the type described.

Also supported by housing 11 on the end wall 11A thereof opposite the upper end containing the extension 11E, are a plurality of receptacles 11B, 11C and 11D for respectively connecting a source of charging current to a rechargeable battery in the housing, a cable conductor for a physiological sensor and a cable extending to an external memory or communication network such as associated with a remote recorder or computer.

Figure 2:
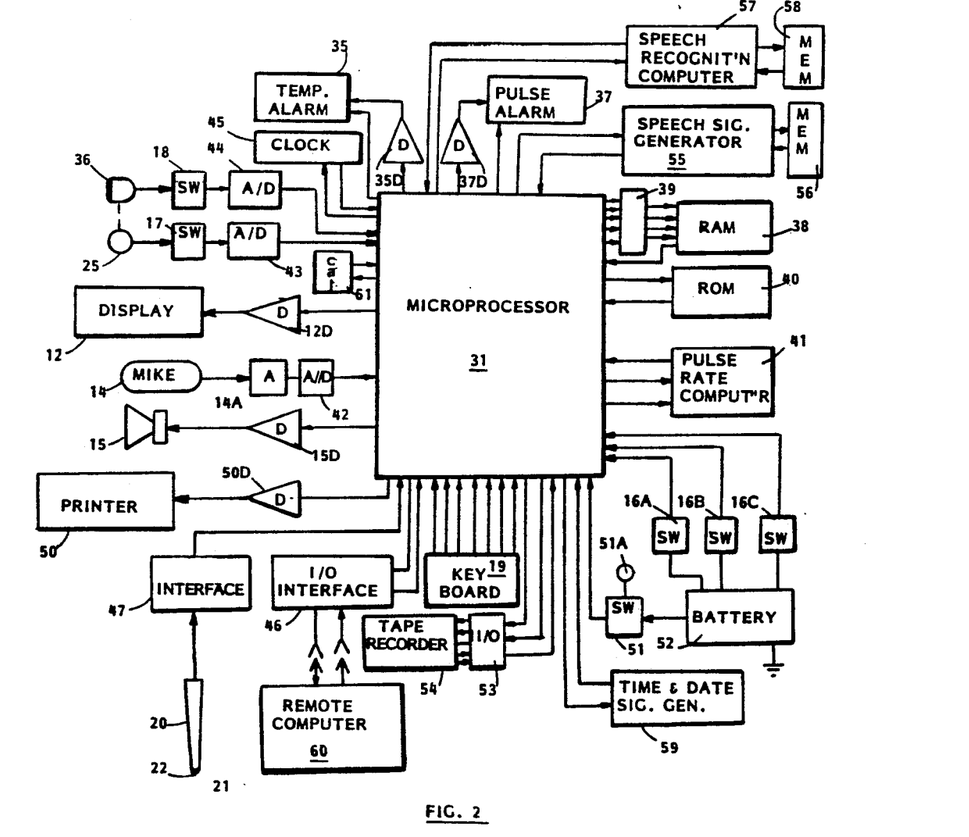
FIG. 2 is a schematic diagram of an electronic system for measuring, computing and recording as well as playing back signals indicative of temperatures measured of a plurality of patients and applicable to the thermometer and recorder of FIG. 1.

A fourth recepticle 11F is shown supported by a side wall 11G of housing 11 and serves to connect one end of a flexible cable 27, extending to a thermometer assembly 23, to computing electronic signal processing, analysing and recording circuitry such as shown in FIG. 2, which is supported within the housing 11. The thermometer sensor assembly 23 includes an elongated rigid tube 24 containing wires (not shown) extending from a sensing head 25 containing an electrically operated temperature sensor, such as a themistor or other form of sensor connected through such wires to respective conductors in a flexible cable 27 to the electronic processing, display and recording circuitry in housing 11. An electrical coupling recepticle 26 at one end of the tube 24 permits the termometer assembly 23 to be changed, while a disposable, thin plastic tube with a closed end (not shown) may frictionally assemble over tube 23 against fitting 26 permitting temperature to be taken therethrough, for hygienic purposes. A male connector 27F at the other end of cable 27 permits such cable to be removably coupled to e receiving female coupling 11F secured to the sidewall of the housing 11.

An elongated opening 28 in a side wall 11S of housing 11, or a hinged door portion of such side wall, is provided to permit a small magnetic tape cassette to be removably inserted into the housing into operative relation with a magnetic recorder and playback unit in the housing, which is not shown in detail but is illustrated in FIG. 2 as operable to receive speech signals generated by microphone 14 when one of the manual switches is closed. Notation 29 refers to an elongaed opening in wall 11S through which a strip of paper 50P from a thermal printer in the housing 11 is driven as it is printed on with characters defining information relating to the physiological variable(s) sensed, the person whose variable(s) are sensed, time and date of such variable sensing, etc. for inclusion with a hard copy record. A bistable on-off switch 51 is also provided supported by the top wall of the housing 11 for connecting a battery therein to the various electrical and electro-mechanical components and subsystems of the measuring instrument. The extension or mount 11E for the light pen is shown secured with a hinge 11H to housing 11 to permit it to be pivoted against the front or rear wall of the housing for convenience in storage or carrying.

In FIG. 2 is shown further details of an electronic control system 30 including the components and electrical circuit elements supported within housing 11 and operable to effect sensing, signal processing, data recording and reproduction and display or intelligible indications of temperature and other physiological variables measured, not only of one but of a number of different patients and not only for one measurement but also for such measurements made over an extended period of time. The system 30 is also operable to record and store data indicative of the physiological measurements made of one or more variables along with data indicative of the identity of each subject or patient whose physiological data is sensed and recorded, as well as the data and time of day each measurement or sensing is taken. Each time a measurement or physiological variable is sensed or a group of such variables is sensed and the resulting signals are electronically processed and recorded, a code or code signals are generated and recorded therewith, to be reproducible therewith, and indicative of the identity of the patient, together with a code or code signals indicative of the date and time of day the sensing and measurement is made.

Such patient identifying codes are generated by causing the light pen 20 to scan a printed bar code, such as one provided on a patient tag or wrist band, bed plate, etc. and/or by selectively operating one or more keys of the keyboard 19. Additional features of the operation of the instrument 10, the control of recording, playback, display, printing and transfer of data to and from the instrument will be described hereafter.

With the exception of externally activated control functions effected by a remote computer 60, to be described, all control functions associated with measurements, recording, visual indication, printing and playback are performed by a microelectronic processor 31, such as the Intel 8086, its equivalent or more advanced microelectronic computer, which controls the operations of the various electronic components and subsystems connected thereto as described. A temperature sensor 25 and a blood pressure or pulse sensor 36 are shown and may be supported adjacent each other on a common mount, such as the end of tube 24, to simultaneously or sequentially sense temperature and pulse or heart beat. Such sensors may also be supported on separate supports to be respectively applied to different, rather than the same, locations of the body of the patient for sensing their respective physiological variables. Manual push-button or membrane switches 17 and 18 respectively connect sensors 25 and 36 to either a common or respective analog-to-digital converters 43 and 44, which transmit digital indications of body temperature and pulse to respective inputs to the microprocessor 31, which, depending on how the keys of keyboard 19 and/or other control switches are operated, records such signals in a memory 38, such as a random access memory or RAM and/or on a select channel or select location of the record tape of a magnetic tape cassette recorder and playback unit 54 through and input-output interface 53 therefore. The microprocessor 31 also signals an electronic clock 59, which is always driven by a battery 52, to cause code signals generated thereby, which are indicative of date and time of day, to be transmitted through the microprocessor to the unit or units recording the sensed data for recording therewith. Indentification of the person whose physiological variable or variables are sensed may be effected by manually scanning a printed patient-code with the light pen 20, by selectively operating one or more keys of the keyboard or by speaking the patient's name or number into the microphone 15 and either recording the analog speech signals generated thereby directly onto a location of the magnetic tape of the recorder 59. Battery 52 is connected through the microprocessor and/or directly to all of the electrically operated components and subsystems of FIG. 2 with the exceptions of a remote computer 60, when on-off switch 51 is manually closed and a small LED lamp 51A connected to such switch is energized when the switch is closed.

While a single membrane or push-button switch 16 is shown in FIG. 1, several switches 16A,16B and 16C are shown in FIG. 2 for controlling the operation of the magnetic tape recorder 54 to cause it to selectively record and playback its recorded data to perform selected of a plurality of functions, defined by the operation of such switches and/or selected switches of the keyboard 19. Such functions may include one or more of the following: (a) The selective operation of electronic display 12 to cause it to display the variable or variables sensed in real time, (b) The selective operation of display 12, through display driver 12D, to cause it to display characters indicative of a (time) selected variable, such as temperature and/or blood pressure or pulse rate taken and recorded the previous time or at any selected past time; (c) the intermittent display at selected time intervals of all recordings of a selected patient derived from memory 37 and/or the recording on the tape of the magnetic tape recorder 54 with or without a displayed indication of the times such variables were measured and/or the dates thereof; (d) the selective operation of display 12 to cause it to display a select of a plurality of different physiological variables, such as temperature, blood pressure, pulse rate, to the exclusion of the others taken, either in sequence over a select time interval or at any select time and date. Similarly, by selectively operating select keys of the keyboard 19, control signals may be generated and employed by the microprocessor 31 for controlling a driver 50D for a printer 50 to cause the latter to print and dispense through opening 29 a strip of paper 50P containing characters indicative of the identity of the patient, one or more physiological variables currently or previously taken and the times and dates they were taken by the instrument.

A synthetic speech signal generator 55, such as the General Instruments Corp. SP-1000 electronic computer, is also shown connected to the microprocessor 31 and, if provided as a microelectronic chip, may be supported in the housing 11 for generating digital signals of speech of one or more words, such as numbers indicative of one or more of the temperatures, blood pressures, pulse rates, etc. taken to be indicated in real time or from signals reproduced from memory or record member as described. The speech synthesizer 55 may supplement the data displayed by the digital display 12 and/or generate sounds of words defining instructions through speaker 15 when applied to a digital-to-analog converter 15D connected to such speaker. Notation 56 refers to an attendant memory for the speech synthesizer 55.

Additional features of system 30 include a temperature alarm 35, which may be manually set, or set by signals generated when select keys of keyboard 19 are operated, to sound an alarm or energize a lamp when the temperature of a person, as it is taken, exceeds and/or falls below select limits. Such temperature alarm is driven by a driver 35D.

Pulse rate is calculated when the output of pressure transducer or microphone 36, which is operatively coupled to a select location of the body of the patient, is passed through switch 18, then to a signal processing unit, such as an analog-to-digital converter 34C which is connected to an input to microprocessor 31, which passes such pulse or pressure signals to a pulse-rate computer 39, having an attendant memory (not shown) containing pulse rate limit recordings for each patient the instrument 10 is employed to measure such variable. Also connected to the microprocessor 31 is a pulse rate alarm/37 driven by an attendant driver 37D for energizing a lamp and/or beeper or tone generator when the pulse rate of a person to whom the transducer 36 coupled, exceed a present rate as programmed in the memory of the computer 39 by the selective operation of the keyswitches of keyboard 19.

Additional features of system 30 include an oscillator clock 45 connected to microprocessor 31 and utilized thereby to provide accurate timing signals for controlling the operation of such devices as memories 37,38, speech signal generator 55, pulse rate computer 39 and any of the other devices requiring proper timing signals, when activated. Notation 47 refers to a control and interface for the signals generated when the light pen 20 is caused to scan printed bar codes.

An external digital computer 60 is shown which is pluggably connected through an input-output interface 46 to the microprocessor 31 to permit data signals recorded in memory 40 and/or magnetic tape recorder 54 to be serially or selectively reproduced and passed to such computer for recording in the memory and use by such computer in recording data for each patient, such as in portions of a memory thereof assigned to each patient. Such data is thus available to medical personnel as hard copy, when selectively reproduced from the memory of the computer and/or to operate a display such as a video display terminal display to generate graphical displays or graphs with suitable peripheral subsystems of the computer. The data recorded in the memory(s) of the instrument 10 may be reproduced and read out to the computer 60 in response to control signals generated by the computer 60 and/or by selectively operating manual switches, such as the switches of keyboard 19 in a manner to cause the microprocessor 31 to address the memory 38 through an address interface 39 to cause it to reproduce all of its recorded information or a select portion of portions of such recorded data.

Also provided in FIG. 2 is a speech recognition computer 57 which may or may not be provided on a single chip, as in the General Instruments Corp. SP-1000. When one of the attendant control switches of the keyboard 19 is activated, speech signals output by the microphone thereafter, such as generated when select words of speech are spoken, are passed to the microprocessor 31 and then to the recognition computer 57, Which when it recognizes select speech signals so generated, generates coded control signals on its output, which may be applied via the microprocessor to control one or more of the described functions such as the operation of the magnetic recorder 54, the display 12, the printer 50, the time and date signal generator 59 and the address unit 39 for the memory 38 to cause all or select signals recorded in such memory to be read out to the microprocessor for use in driving the display, printer, recorder, etc. In other words, the speech recognition computer 57 may be employed in lieu of manually operating the keys of the keyboard 19 or to supplement its operation with certain speech controlled functions of those described above.

Also provided in FIG. 2 is a calibration electronic circuit 36, which may be in the form of logical microelectronic circuitry connected for two-way communication with the microprocessor 31 and operable under the control of the microprocessor to analyze signals generated by the temperature transducer 25 when it is first energized after switches 17 and 51 are activated, for the purpose of calibrating the thermometer. Such calibration may be effected in accordance with signals generated by a second temperature sensor (not shown) mounted either adjacent the sensor 25 or on the housing 11, wherein the calibration circuitry 36 compares the two signals and generates output code signals which may be applied to the display 12 and/or to any of the auxilliary indicators. For example, a code or signals output by calibration circuitry 36 may be applied to the sythetic speech signal generator 55 to cause it to generate speech signals of a word or words indicative that the thermometer is or is not properly calibrated. Such code output by the calibration circuitry 36 may also be used applied to effect proper calibration of the thermometer by means of suitable receiving and calibrating circuitry in the microprocessor or connected thereto.

Figure 3:
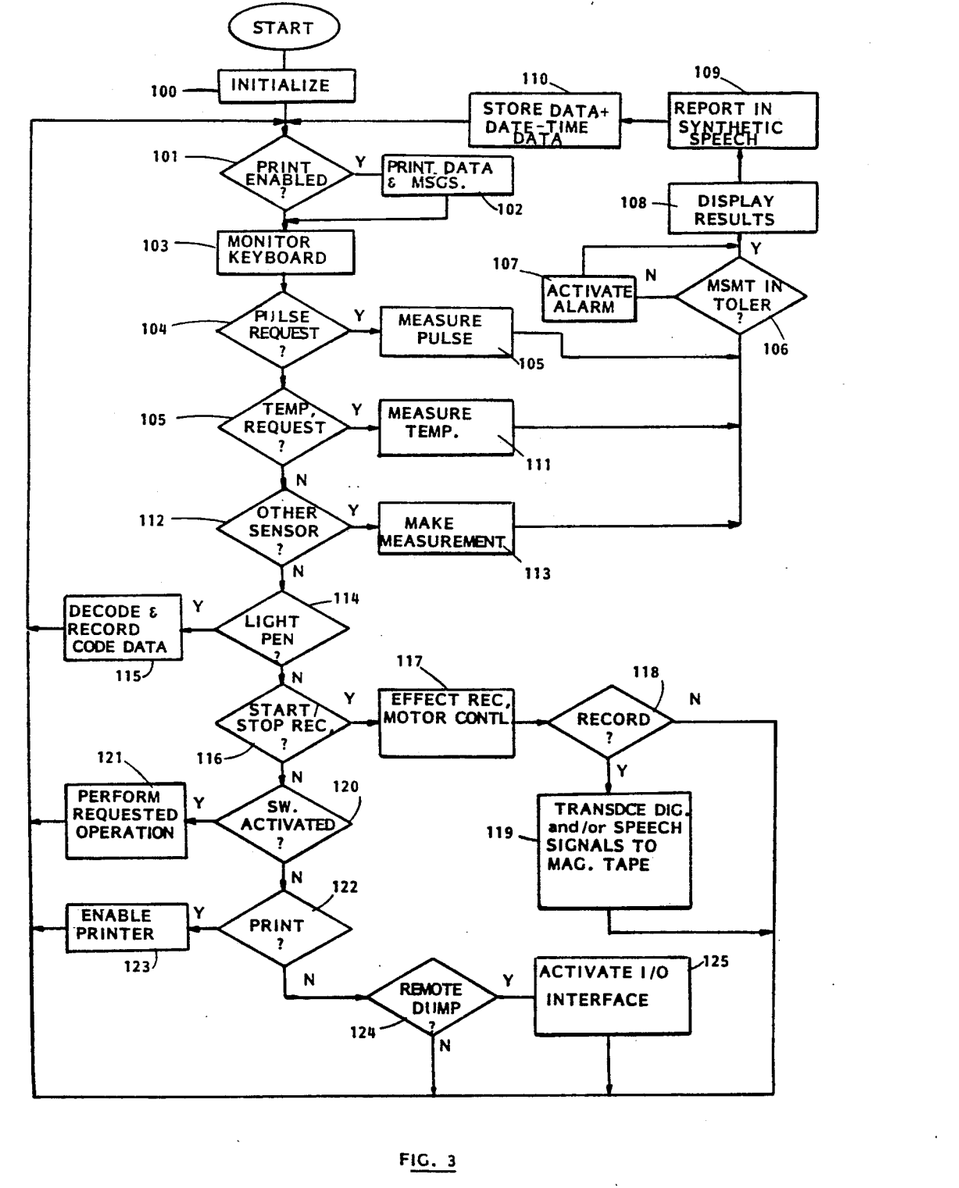
FIG. 3 is a flow diagram showing steps in the operation of the thermometer of FIG. 1 and the system shown in FIG. 2.

FIG. 3 is a functional or flow chart representation of operational steps possible during the operation of system 30. On power-up, system 30 is initialized at point 100 with execution continuing at step 101 where a print-enable request is checked. For subsequent operation, if hard copy printing is enabled, current data recorded in the data memory 38 is applied to cause the printer 50 at step 102 to print characters defining such data. Thereafter control passes to step 103 where the operation of the keyboard is monitored. If a valid command is effected by the manual operation of selected keys of the keyboard, control passes to step 104. If such keyboard operation is to measure pulse rate, flow passes to step 105 at which pulse sensing is effected and time averaged with processing continuing at step 106. At step 106 the pulse rate calculated is compared with acceptable pulse limits from recordings in the memory of pulse rate computer 41. If the pulse rate computed is in bounds, execution continues with display of such pulse rate effected by step 108. After display of such pulse rate control passes to step 109 at which the synthetic signal generator 55 is employed to audibly indicate the measured results. Execution then proceeds to step 110 at which the data relating to the measurement or measurements made is stored in memory 38 with data relating to date, time and patient identification whereafter control returns to point 101.

If, at point 104, pulse rate measurement request is not detected, control passes to point 105 to detect a temperature taking request. If temperature measurement is requested, control passes to point 111 at which a temperature measurement is made and averaged, whereafter such temperature measurement is indicated on the display and/or by synthetic speech and is stored in step 110, as described, for the recording of pulse rate data in memory 38. If at point 105, temperature measurement is not requested, execution continues to step 112 at which one or more other valid physiological parameter sensor measurements, such as EKG, biological variables associated with an electrode, light beam sensor or other sensor, are taken after the computer or controller 31 checks input commands generated by select speech signal recognition or keyboard operation. If a valid command, thus generated, is thus recognized, control passes to step 113 where such measurement is made. Execution then continues in steps 106 to 110, as described, for such auxilliary measurement or measurements made. If at step 112, no measurement request or command is recognized, flow proceeds to step 114 where light pen operation is checked. If a bar code reading with the light pen 20 is requested, control passes to step 115 where the code signals generated by the light pen in scanning a printed bar code on a tag or sheet associated with the patient is decoded and the patient identification code and/or other data so generated, is recorded in memory 38, as described, whereafter execution returns to point 101. If such a light pen request is not recognized, control passes to point 116 at which requests for the operation of the tape recorder 54 are recognized. If such a request is recognized, control passes to step 117 at which tape recorder motor or motors are started and control passes to point 118 at which control is checked to determine if a recording command is present. If such is detected, control passes to step 119 where the current measurement(s) data, together with date and time data from the clock or signal generator 59 are recorded as digital code or record signals on one track of the magnetic tape of the recorder while, any audio speech signals generated on the output of the microphone 14 are recorded on another track of the magnetic tape. If, at point 119, no command to record data is detected, control is returned to a point between points 100 and 101.

If at point 116, no command to operate the tape recorder is detected at all, control passes to point 120, where the operation of manual control switches 16, 17 and 18 is monitored. If any of such switches have been activated, control passes to point 121 at which the corresponding system function or functions are immediately performed whereafter execution returns to point 101.

If at point 122, a print command is not recognized, control passes to point 12 where commands relating to the dumping or transmission of measurement recordings to external computer 60 are recognized. If a printer activation command is recognized, control passes to point 123 at which the printer operation is enabled to effect printing, printout is effected and then the printer is deactivated after which control passes to point 101.

If, at point 122, a print command is not recognized, control passes to point 124 commands relating to the dumping of recordings in the memory 38 and/or magnetic tape of the recorder 54 into an external memory or computer are recognized and control passes to point 125 where the input-output interface 46 is activated and the contents of such memory and/or recorder are reproduced therefrom and transmitted to the external system. If no such request is recognized at point 122 control returns to point 101.

Modifications to the temperature sensing and recording instrument and system illustrated in FIGS. 1 to 3 are noted as follows:

a) All or selected portions of the temperature and/or pressure data recorded in the RAM memory 38 may be selectively reproduced therefrom in a sequential manner to perform one or more of the functions of driving and causing the printer 50 to serially print such data on the paper strip 50P; drive the display 12 to cause it to display a select temperature or pressure or a select series of temperatures of a select living being or a select number of living beings wherein either the microprocessor 31 or an auxilliary timing control circuit (not shown) controls the timing of each display of temperature or pressure; controlling the speech signal generator 55 to cause it to generate select synthetic speech signals which, when applied to the speaker, generate sounds of words of speech defining a select temperature taken at a select time of a select living being; reproduce code signals defining all temperature readings taken and recorded or select temperatures, such as those taken of select persons, at select times or dates or temperatures recorded over a select period of time, for presentation to the interface 46 and transmission therefrom via wire or short wave means to a remote recorder or computer. Such selective data playback from memory 38 may be effected by generating suitable address codes by the selective manual operation of the keyboard 19, by speaking selected words of speech into the microphone 14 after operating a selected control switch or switches of the keyboard, by causing the light pen 20 to scan a select printed (bar) code after selectively operating a control switch such as one or more switches of the keyboard 19, by the remote generation and transmission of selected control code signals through the input-output interface 46 to the computer or microprocessor 31 to effect such control and playback from the memory 38, or by a combination of control signals generated by two or more of such control means or input devices.

b) The four data selection code signal generating subsystems described above for selectively addressing the memory 38 to cause it to reproduce selected data recorded therein, may also be employed to selectively reproduce data and speech signals recorded in the magnetic recorder 54 by controlling the operation of such recorder using circuits of the microprocessor 31 or auxilliary comparator circuitry connected thereto for comparing address codes generated by the keyboard 19, the lightpen 20, the speech recognition computer 57 or the remote computer 60 with code signals reproduced from the tape of the recorder 54 and generating corresponding reproduction control signals after the microprocessor or computer 31 has controllably started the recorder by operating its tape drive motor(s). For example, the keyboard, light pen or computers 57,60 may be operated to generate a code signal similar to the patient identification code signal recorded with each temperature and/or pulse rate recording and such code signal may be applied to an electronic comparator receiving reproductions of codes from the magnetic tape. Each time a comparison or coincidence is detected, the temperature indicating signals reproduced therewith or therefollowing are reproduced and transmitted to the selected interface or drive.

c) The control circuitry denoted 39 may comprise an intelligent input-output interface or address for controlling the recording of data in the memory 38, whereby such data is gated to select locations of such memory to permit it to be selectively reproduced by addressing selected blocks of the memory, according to subject such as patients whose temperatures are taken, dates and/or select time intervals. Thus when select address codes are generated and applied to the input of the intelligent address circuitry 39, data recorded in respective select portions of the memory is read out and applied through the microprocessor 31 to one or more select drives or interfaces of the system 30.

d) Two or more lines of the display 12 may be simultaneously activated with data obtained from the memory 38 and/or signal processing circuits including the analog-to-digital conversion circuits 43,44 and the circuitry of the microprocessor 31 employed to calculate temperature and the pulse rate computer 41, to simultaneously display characters indicative of instantaneous temperature and pulse rate taken and calculated or past temperature and pulse rates as defined by the selective operation of one or more of the address signal generating devices 19,20,59, etc.

e) Notation 61 refers to a temperature calibration circuit shown connected for two way communication with the microprocessor 31 to permit periodic automatic and/or user activated calibration of the temperature sensor 25. Such calibration may be effected by electronic signal analysis and/or by applying a known current to a small resistor located adjacent the temperature sensor or thermistor 25, for a short select period of time under the control of the microprocessor 31 which gates the resulting output of the sensor to a signal comparator in the circuit 61 or the microprocessor 31.

f) The pulse rate computer 41 may be made in accordance with the teachings of U.S. Pat. No. 3,978,848 as well as other patents while temperature signal processing and display means are disclosed insuch U.S. Pat. Nos. as 4,428,684; 4,397,569; 4,286,465 and others such as the references therefor.

g) In an modified form of the embodiment shown in FIG. 1 it is noted that the temperature and/or pressure or body sound sensor(s) may be supported by the housing extension 11E as a replacement for the sensor 20 or by another portion or extension of the housing 11 adapted to be inserted in the mouth under the tongue of a living being. Suitable disposable thin walled plastic tubular covers may also be provided to be placed over the temperature and/or pressure sensor(s) and the tubular support therefore for hygienic purposes, wherein such covering means is shaped and thin enough to permit suitable body temperature and pulse sensing to be effected by the sensor(s) surrounded thereby.

g) The pressure sensor 36 may comprise or be supplemented with a sound detector, such as a microphone for detecting body sounds while in contact with the skin. By suitably computer analysis of the resulting sound signals output by such microphone both heart pulse and other body sounds may be analyzed for diagnostic purposes. Such signal analysis may be provided in the computer or microprocessor 31, one or more auxilliary signal analyzing circuits connected for two way communicatio therewith and/or the remote computer 60.

h) Heart pulse may be sensed by suitable photo-optical sensing means supported, for example, on its own support similar to rigid tube 24 which is connected by cable to circuitry in the housing 11 including microprocessor 31, for processing and analyzing the output of a photodetector receiving light from an adjacent light source after it pass passed through and reflected from blood flowing through an artery near the surface of the skin of a person against which such sensing means is disposed. Such photoelectric sensing means may also be supported adjacent the temperature sensor 25 on its mount.

i) For certain physical or physiological measurements, such as those involving body sounds and the like for diagnostic purposes, a sensitive microphone may be supported at the end of the probe or instrument arm or support 24 and utilized per se or in combination with one or more of the sensors described to sense and provide variable electrical signals indicative of body sounds and vibrations which signals, by the application of suitable signal analysis thereof, may be employed to diagnose or indicate that further testing is needed to diagnose one or more of a number of human maladies such as associated with the circulatory and respiratory systems. Such body sound sensing may be effected when such sensitive microphone is applied to one or more locations of the body, such as the external skin and/or within one or more body cavities in a body sound detection and sampling procedure carried out to simultaneously and/or sequentially detect sounds associated with blood pulsing and flow, breathing or respiration, muscular activities and body tremors induced and caused by neuromuscular activity resulting from a disease, deficiency or other malady. When such a sensitive microphone is employed per se or in combination with one ore more additional sensors, such as a temperature sensor, a cancelling microphone may also be employed supported on the elongated support 24 or housing 11, to pick up ambient sounds, generate corresponding signals thereof and apply same to the recorder or signal processor processing the body sound sensor to cancel or eliminate such ambient sounds as generated by speech, room sounds, or the like, from the signal processing and analysis to facilitate analyzing the body sound generated signals.

What is claimed is:

1. A portable electronic thermometer in accordance with claim 1 wherein said third means is supported by said portable housing and includes a microphone for receiving sounds of select speech spoken in the vicinity of said housing, electronic speech recognition computing means within said housing and connected to receive, process and analyze the speech signals output by said microphone and generate respective coded electrical signals, said third means also including a memory containing recordings of codes indicative of the identity of a plurality of living beings whose temperatures are periodically caused to be sensed by said first means and means for addressing said memory with coded electrical signals generated when said speech recognition computing means recognizes select speech spoken into said microphone to cause select code signals to be generated on the output of said memory and to be recorded in said memory of said fifth means along with respective codes representative of temperatures generated on the output of said third means.

* * * * *

UNITED STATES PATENT AND TRADEMARK OFFICE
CERTIFICATE OF CORRECTION

PATENT NO. : 5,181,521
DATED : January 26, 1993
INVENTOR(S) : Jerome H. Lemelson It is certified that error appears in the above-indentified patent and that said Letters Patent is hereby corrected as shown below:

On the title page, the inventor's city of residence should be changed from "Princeton, N.J." to —Incline Village, Nev.—

Signed and Sealed this

Eleventh Day of April, 1995

Attest:

BRUCE LEHMAN

Attesting Officer

Commissioner of Patents and Trademarks